(12) United States Patent
Gill (10) Patent No.: US 8,442,653 B2
(45) Date of Patent: May 14, 2013

(54) BRAIN ELECTRODE

(75) Inventor: Steven Streatfield Gill, Bristol (GB)

(73) Assignee: Medtronic, Inc., Minneapolis, MN (US)

( * ) Notice: Subject to any disclaimer, the term of this patent is extended or adjusted under 35 U.S.C. 154(b) by 137 days.

(21) Appl. No.: 13/019,670

(22) Filed: Feb. 2, 2011

(65) Prior Publication Data

US 2011/0131808 A1  Jun. 9, 2011

Related U.S. Application Data

(63) Continuation of application No. 10/469,423, filed as application No. PCT/GB02/00851 on Feb. 26, 2002, now abandoned.

(30) Foreign Application Priority Data

Feb. 28, 2001  (GB) ................................. 0104982.4

(51) Int. Cl.
*A61N 1/375* (2006.01)

(52) U.S. Cl.
USPC ....................................................... 607/116

(58) Field of Classification Search ............ 607/116
See application file for complete search history.

(56) References Cited

U.S. PATENT DOCUMENTS

| | | |
|---|---|---|
| 4,458,695 A | 7/1984 | Peers-Trevarton |
| 4,819,647 A | 4/1989 | Byers |
| 4,848,352 A | 7/1989 | Pohndorf |
| 4,961,434 A | 10/1990 | Stypulkowski |
| 5,000,194 A | 3/1991 | Van den Honert |
| 5,374,285 A | 12/1994 | Vaiani |
| 5,423,877 A | 6/1995 | Mackey |
| 5,455,998 A | 10/1995 | Miyazono |
| 5,517,989 A | 5/1996 | Frisbie |
| 5,524,338 A | 6/1996 | Martyniuk |
| 5,562,722 A | 10/1996 | Racz |
| 5,649,970 A | 7/1997 | Loeb |
| 5,686,516 A | 11/1997 | Tzur |
| 5,800,465 A | 9/1998 | Thompson |
| 5,843,093 A | 12/1998 | Howard, III |
| 5,843,148 A | 12/1998 | Gijsbers |
| 5,895,416 A | 4/1999 | Barreras, Sr. |
| 5,913,882 A | 6/1999 | King |
| 5,991,650 A * | 11/1999 | Swanson et al. ............. 600/374 |
| 6,038,480 A | 3/2000 | Hrdlicka |

(Continued)

FOREIGN PATENT DOCUMENTS

| | | |
|---|---|---|
| EP | 0 580 928 | 2/1994 |
| EP | 1 048 317 | 3/2003 |

(Continued)

OTHER PUBLICATIONS

Xu et al., Comparison of Half-Band and Full-Band Electrodes for Intracochlear Electrical Stimulation, Ann Otol Rhinol Laryngol pp. 363-367, 102:1993.

(Continued)

*Primary Examiner* — Eric D. Bertram (74) *Attorney, Agent, or Firm* — Mueting Raasch & Gebhardt PA (57) ABSTRACT

An electrode, in particular a deep brain stimulating (DBS) electrode or a deep brain lesioning electrode, a method for manufacturing an electrode and use of the electrode, and a directional electrode.

15 Claims, 4 Drawing Sheets

U.S. PATENT DOCUMENTS

| | | | |
|---|---|---|---|
| 6,052,624 | A | 4/2000 | Mann |
| 6,064,905 | A * | 5/2000 | Webster et al. ............... 600/424 |
| 6,106,522 | A * | 8/2000 | Fleischman et al. ............ 606/41 |
| 6,319,241 | B1 | 11/2001 | King |
| 6,473,653 | B1 | 10/2002 | Schalhorn |
| 6,510,347 | B2 | 1/2003 | Borkan |
| 2002/0183817 | A1 | 12/2002 | Van Venrooij |
| 2003/0083724 | A1 | 5/2003 | Jog |
| 2004/0098074 | A1 | 5/2004 | Erickson |

FOREIGN PATENT DOCUMENTS

| | | |
|---|---|---|
| EP | 0 832 667 | 2/2004 |
| WO | WO 99/43031 | 8/1999 |
| WO | WO 02/45795 | 6/2002 |

OTHER PUBLICATIONS

Jansen, Henri et al., A Survey on the Reactive Ion Etching of Silicon in Microtechnology, J. Micromech. Microeng. 6:14-28 (1996).

* cited by examiner


BRAIN ELECTRODE

CROSS REFERENCE TO RELATED APPLICATIONS

This patent application is a continuation application of U.S. patent application Ser. No. 10/469,423 filed Aug. 20, 2004, which is a National Phase filing of PCT/GB02/00851 filed Feb. 26, 2002, which claims the benefit of priority of Great Britain Patent Application No. 0104982.4, filed Feb. 28, 2001, all of which are incorporated herein by reference.

TECHNICAL FIELD

The present invention relates to an electrode, in particular a deep brain stimulating (DBS) electrode or a deep brain lesioning electrode. The present invention also relates to a method for manufacturing the electrode of the present invention and the use of the electrode.

BACKGROUND

Stimulating and lesioning electrodes are used in a variety of surgical procedures, in particular, DBS electrodes are used in a variety of neurosurgical procedures.

A surgeon wishing to stimulate or lesion a particular area of nervous tissue, can target the end of an electrode to the target site so that a desired electrical current can be delivered. Numerous methods are known for targeting the electrode to the desired site including stereotactic methods.

Generally, deep brain stimulating electrodes are manufactured by forming a coil of one or more insulated wires having non-insulated ends on a support, welding electrode conducting areas on to the non-insulated ends of the wires and placing a sheath of non-conducting material over the non-conducting parts of the electrode. It is clear that such a method for producing an electrode is laborious and therefore expensive.

Furthermore, as numerous parts are used in the construction of the electrode, it is possible that the overall diameter of the electrode will vary along its length. In particular, the electrode areas which are welded on to the electrode, especially to spot weld points, can be proud of the rest of the surface of the electrode leading to difficulties in inserting the electrode. A further problem with electrodes constructed in this manner is that the electrode has to be of a sufficient size for it to enable electrode conducting areas to be welded onto the non-insulated ends of the wires.

There is therefore a need in the art for an electrode which can be constructed more efficiently and with greater accuracy.

It is becoming increasingly common for patients with disorders of brain function, including disorders of movement, intractable pain, epilepsy and some psychiatric disorders to be treated with deep brain stimulation. DBS electrodes are chronically implanted into the fine targets in the brain where electrical stimulation will disrupt abnormal neural firing in these patients to alleviate their symptoms. Brain targets for treating functional disorders are usually deeply situated and of small volume. For example, the optimum target for treating Parkinson's disease is situated in the sub-thalamic nucleus (STN) and is a sphere of 3 to 4 mm in diameter or an ovoid of 3 to 4 mm in diameter and 4 to 5 mm in length. Other targets such as the globus pallidus (used for treating hyper- or hypo-kinetic disorders) or targets in the thalamus (used for treating tremor) are usually no more than 1 to 2 mm larger.

Current DBS electrodes, for example those supplied by Medtronic Inc, Minneapolis, Minn., are of dimensions to accommodate such volumes. For example, such electrodes have a diameter of about 1.27 mm and have 4 ring electrodes of the same diameter positioned at their distal end. Each ring electrode has a length of 1.5 mm with a 1.5 or 0.5 mm separation. In use, the DBS electrode is connected to a battery driven pulse generator via a cable and the equipment implanted subcutaneously, generally with the pulse generator positioned below the clavicle. The frequency, amplitude and pulse width of the stimulating current delivered to the electrode contacts can be programmed using external induction.

Figure 4:
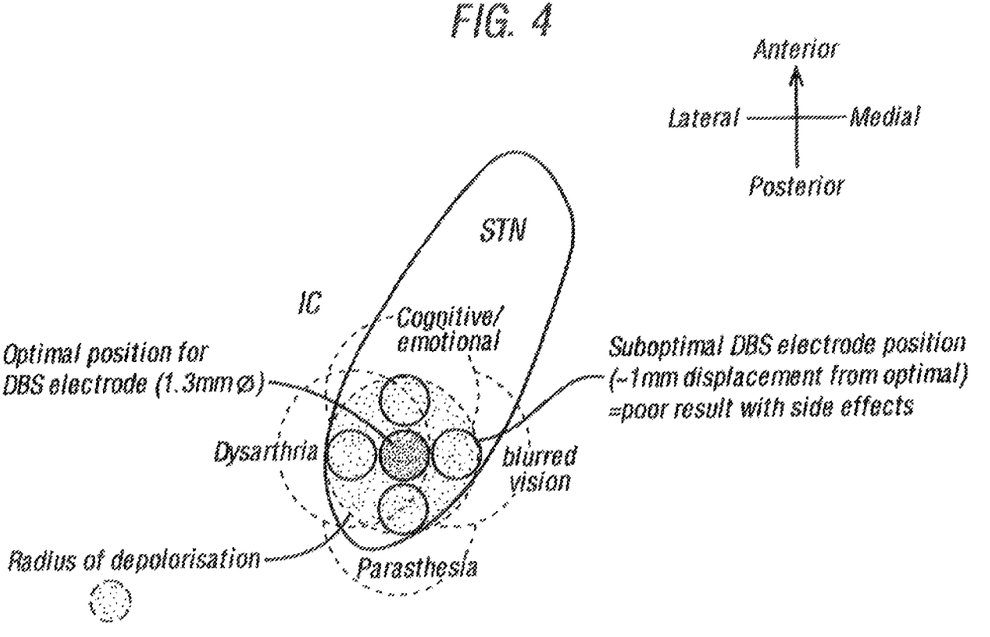
FIG. 4 shows a schematic view of a desired target site and shows optimal and sub-optimal positions of an electrode.

A problem with the use of such electrodes is the difficulty in accurately placing the electrode within the desired target. The accuracy of placement is key to the effectiveness of the treatment. For a small target such as the STN, misplacement of the electrode by no more than 1 mm will not only result in sub-optimal symptomatic control but may induce unwanted side effects such as weakness, altered sensation, worsened speech or double vision (see FIG. 4).

The established method to place an electrode into a functional brain target is first to localise the area of abnormal brain function. This is achieved by fixing a stereotactic reference frame to the patient's head, which can be seen on diagnostic images, and from which measurements can be made. The stereotactic frame then acts as a platform from which the electrode is guided to the target using a stereoguide that is set to the measured co-ordinates.

However, functional neurosurgical targets are often difficult or impossible to visualise on diagnostic images and so their actual position may need to be inferred with reference to visible land marks in the brain and using a standard atlas of the brain to assist the process. Due to anatomical variation between an individual and the atlas and even between different sides of the same brain in an individual such differences can lead to error in target localisation. Errors in target localisation may also result from patient movement during image acquisition or geometric distortion of images which can be intrinsic to the imaging methods. Such errors may be further compounded at surgery by per-operative brain shift. This may result from the change in head position from that during image acquisition to the position on the operating table, from leakage of cerebrospinal fluid when a burr hole is made with subsequent sinking of the brain and/or from the passage of the electrode through the brain substance. Surgeons attempt to correct these errors by performing per-operative electro-physiological studies on the patients undergoing functional neurosurgery who are kept awake during the procedures. These studies include microelectrode recording of the neural firing in the planned target area and/or stimulation of the target area using a test electrode. A series of passes are made through the target area with microelectrodes and sample recordings taken. The target is defined by its characteristic patterns of firing. Because of the jelly-like consistency of the brain and the depth of the functional targets within it, there needs to be a space of about 2 mm between different microelectrode passes to prevent the electrode passing down a previously made track. Thus, for a small target such as the STN, it is possible for the recordings from two microelectrode passes, 2 mm apart, to both register location within the target structure but to find neither of them to be optimally located centrally within the target. Likewise, if a test stimulation electrode is passed just off the optimal target position, i.e. .+−.1 millimeter, then a second pass to correct this error will almost inevitably result in the electrode passing down the same track.

If an electrode is placed exactly in the centre of a target having a 3 mm diameter, then the distance from the electrode surface to the edge of the target is usually under 1 mm. If the current spreads beyond this, then side effects can be incurred.

For these reasons, given the small chance that an electrode will be placed in the centre of a target and that a placement error of .+−.1 mm can result in sub-optimal treatment with side effects, which cannot readily be corrected with repositioning, there is a need for an electrode which overcomes at least some of these problems.

U.S. Pat. No. 5,843,148 discloses a high resolution brain stimulation lead, wherein the electrode comprises ring segments diagonally arranged along the circumference of the lead. Accordingly, in theory by passing a stimulation current between electrode contact areas (i.e. ring segment), off axis stimulation can be achieved. Off axis stimulation refers to the generation of an electric field that is displaced to one side of the electrode. Furthermore, by rotating the lead, different volumes of tissue around the lead circumference may be stimulated. The major problem with this device is that the diagonal geometry of the ring segment results in a complex electric field which will spiral around the portion of the diameter of the electrode and is necessarily elongated along the axis of said electrode. The proposed configuration would therefore not form an off axis electric field that is suitable for treating a desired target. Furthermore, this device does not enable one skilled in the art to adjust the volume of tissue being stimulated in both the axial plane and the horizontal plane independently. Instead, on rotating the electrode, the volume of tissue stimulated varies in both the horizontal and axial planes, making interpretation of patient's responses extremely difficult. Furthermore, the complex geometry of the proposed electrode would be difficult to construct and vulnerable to mechanical failure.

There is therefore a need for an electrode which overcomes at least some of the problems associated with the prior art electrodes.

SUMMARY

In a first embodiment of the present invention there is provided an electrode having a proximal and distal end comprising a core comprising:
(a) one or more insulated wires extending from the proximal end to the distal end wherein the one or more insulated wires have non-insulated ends, present at the proximal and distal ends;
(b) an insulating sheath around the core, wherein the non-insulated ends of the one or more wires are not covered by the insulating sheath; and
(c) one or more electrode conducting areas formed by depositing electrically conducting material on the surface of the sheath, wherein the one or more electrode conducting areas are in electrical contact with at least one of the a non-insulated ends of the one or more insulated wires.

The term "electrode" refers to any electrical conducting lead for enabling the production of an electric field at a desired site. Preferably the electrode is a DBS or deep brain lesioning electrode. Such electrodes are well known to those skilled in the art. The one or more insulated wires are arranged so that an electric current can be passed from the proximal end of the electrode to the distal end of the electrode. Preferably a separate electrode conducting area is formed for the end of each one or more insulated wires at the distal end of the electrode. By making an electrical connection to the corresponding end of the wire at the proximal end, the electrode conducting area will be electrically charged. Preferably electrode conducting areas are present at one or both ends of the electrode.

The term "insulated" as used herein means electrically insulated. The insulated wires used in the electrode of the present invention can be any insulated wires. Preferably the insulated wires are made from gold, a gold alloy or a platinum/iridium alloy.

It is further preferred that the core of the electrode comprises a plurality of the insulated wires. It is particularly preferred that the core comprises 3 or 4 insulated wires.

The insulating sheath can be made from any non-conductive material, preferably a plastics material. In particular, it is preferred that the insulating sheath is made from polyurethane.

The purpose of the electrode of the present invention is to produce an electric field at a desired target site. The electrode has a proximal end which, in use, is connected to an electricity source. The proximal end is preferably connected to the electricity source by the one or more electrode conducting areas present at the proximal end of the electrode. Preferably each electrode conducting area at the proximal end is connected to an electrode conducting area at the distal end of the electrode via an insulated wire. Electrode conducting areas at the distal end are positioned, during use, at the target site and an electric field is produced. Depending on the electrical connections made at the proximal end, the electric field will be generated by corresponding electrode conducting areas present at the distal end. Accordingly, it is possible to produce an electric field with different electrode conducting areas and furthermore it is possible to generate either a mono-polar or bi-polar electric field. Altering the connections of an electrode to an electric source is well known to those skilled in the art. In particular, the technical manual for Medtronic's DBS leads 3389 and 3387 clearly discusses changing electrical connections at the proximal end of an electrode to change the electric field generated at the distal end of the electrode.

The electrode of the first embodiment of the present invention is preferably less than 2 mm in diameter, more preferably less than 1.5 mm in diameter, most preferably 1.27 mm in diameter. The electrode can be of any length and is preferably between about 10 cm and 30 cm in length. The length of the electrode will vary depending on the distance of the desired target from an accessible surface of the patient.

The electrode conducting areas formed on the electrode can be any desired shape. Preferably the electrode conducting areas are formed as annular rings around the electrodes. For producing a directional electric field areas such as squares or rectangles can be formed on a part of the circumference of the electrode. Preferably each electrode conducting area extends over less than half, more preferably less than a quarter and most preferably between about an eighth and a sixteenth of the circumference of the electrode by restricting the size of electrode conducting area. By restricting the area of the electrode conducting area it is possible to produce a directional electrical field as is discussed in greater detail below.

Preferably the electrode conducting area is positioned on the electrode so that its longitudinal axis is parallel to or perpendicular to the longitudinal axis of the electrode. By ensuring that the electrode conducting area is so orientated it is possible for the surgeon to determine the effects of moving the electrode with greater ease.

Preferably the electrode conducting areas are rectangular in shape and the longitudinal axis of the rectangle is parallel to the longitudinal axis of the electrode. It is further preferred that the rectangles are about 1.5 to 3 mm in length and about 0.2 to 0.5 mm in width. If there is more than one electrode conducting area present on the electrode the electrode conducting areas are preferably arranged in a line parallel to the longitudinal axis of the electrode (See FIG. 5). Alternatively, it is preferred that each electrode conducting area is staggered along the length of the electrode (see FIG. 6A). By ensuring that the electrode conducting areas are staggered, it again allows greater flexibility to the surgeon for producing the electric field at different positions along the length of the electrode on which the electrode conducting areas are positioned.

The electrically conducting material can be any material suitable for forming an electrode conducting area including metals, polymers etc. Preferably the electrically conducting material is gold or platinum.

The one or more electrode conducting areas can be formed by any method. Preferably, the electrode conducting areas are formed by depositing electrically conducting material of the surface of the sheath. There are numerous methods well known to those skilled in the art for depositing electrically conducting material on the surface of various materials. Preferably the electrically conducting material is deposited by jet printing, etching, photolithography, plasma deposition, evaporation, electroplating, or any other suitable technique.

Jet printing techniques are well known to those skilled in the art. For example, in U.S. Pat. No. 5,455,998, an ink jet head for depositing conductive ink onto a desired surface is disclosed. U.S. Pat. No. 5,114,744 discloses a method for applying a conductive material to a substrate using an ink jet. Furthermore, WO 99/43031 discloses a method for depositing by ink jet printing an electrode layer onto a device.

Etching methods for depositing electrically conducting material are also well known to those skilled in the art. In particular, such methods are described in Plasma Etching in Microtechnology, Universiteit Twente, Fluitman and Elwenspoek, ISBN: 103650810x. See also Jansen et al, Journal of Micromechanics and Microengineering, 14-28, 1996.

Photolithography techniques are also well known to those skilled in the art and are described in Geiger et al, VLSI, Design Techniques for Analogue and Digital Circuits, Chapter 2, 1990.

WO 90/33625 describes a process for depositing a conductive layer on a substrate comprising depositing ink on the substrate by means of lithographic printing to form a seeding layer and then depositing an electrically conducting layer.

There are numerous deposition techniques including evaporation, sputtering and vapour deposition. All these methods are described in VLSI Design Techniques for Analogue and Digital Circuits (supra).

Electroplating techniques are well known to those skilled in the art and have been used for depositing electrically conductive material at a desired site on numerous materials.

A further method by which it is possible to deposit electrically conducting material is by using conductive spray paint. Conductive spray paint may be used in combination with an ink jet printing head. Furthermore, companies such as Precision Painting, Anaheim, Calif., have been applying electrically conductive coatings such as copper and nickel to a variety of objects. Accordingly, such methods can be used in order to provide an electrically conducting material to a desired substrate.

By depositing electrically conducting material on the surface of the sheath, the electrode can be produced easily and inexpensively as it is no longer necessary to weld the electrically conducting parts to the non-insulated ends of the wires.

The electrode of the first embodiment of the present invention is robust as it does not comprise welded contacts. Furthermore, by depositing the electrically conducting material using the methods described above, it is possible to produce the electrode conducting areas precisely and in virtually any size and shape. Furthermore, the electrically conducting material can be deposited as a thin coating ensuring that the diameter of the electrode does not increase significantly and therefore does not affect the insertion of the electrode. The electrodes can also be made very small (less than 1 mm in diameter) because it is not necessary to spot weld electrode conducting areas on to the electrode.

In a further preferred embodiment the electrode according to the first embodiment of the present invention may have a flexible distal end allowing the distal end to be bent, using for example a J wire, so that it can be moved to a desired position.

The present invention also relates to a method for constructing an electrode according to the first embodiment of the present invention comprising:
   coating a core comprising one or more insulated wires with an electrically insulating sheath, wherein the non-insulated ends of the one or more wires are not coated by the sheath; and
   depositing electrically conducting material on the surface of the sheath to form one or more electrode areas which are in electrical contact with at least one of the non-insulating ends of the one or more insulated wires.
   Preferably, the core is formed by winding the one or more insulated wires around a supporting member. Preferably the supporting member is a tungsten wire. The supporting member is removed one the electrode is formed.

The electrically conducting material can be deposited by any method, including jet printing, etching photolithography, plasma deposition, evaporation and electroplating.

The present method is a simple and efficient method for the production of electrodes and allows greater flexibility in the production of the electrode conducting area on the electrode.

The method of the present invention can be automated to further reduce the cost of producing the electrode.

In the second embodiment of the present invention, there is provided a directional electrode having a proximal end and a distal end comprising:
   (a) a core comprising one or more insulated wires extending from the proximal end to the distal wherein the one or more insulated wires have non-insulated ends present at the proximal and distal ends;
   (b) an electrically insulating sheath around the core, wherein the non-insulating ends of the one or more wires are not covered by the insulating sheath; and
   (c) one or more electrode areas in electrical contact with at least one of the non-insulated ends of the wire, wherein each electrode area extends over less than half the circumference of the electrode.

The term "directional electrode" refers to an electrode which produces an electric field that it is not uniformly formed around the circumference of the electrode. Instead the electric field is displaced to one side of the electrode. By having an electric field displaced to one side of the electrode, it is possible to change the position of the electric field by rotating the electrode. This has the advantage that when the electrode is placed in a sub-optimal position, it is possible to rotate the electrode and thereby alter the position where the electric field is produced relative to the target tissue, resulting in increased flexibility of the system and enabling the production of an electric field at an optimal position relative to the desired tissue.

By ensuring that the electrode conducting area extends over less than half the circumference of the electrode, it ensures that the electric field is displaced to one side of the electrode. Preferably, the electrode conducting area extends over less than a quarter, more preferably between about an eighth and a sixteenth of the circumference of the electrode. The smaller the electrode conducting area, the greater displacement of the electric field generated. However, if the electrode conducting area becomes too small (less than a sixteenth) it is possible that the electric field becomes toxic and causes tissue death using conventional current supply levels. Accordingly, the amount of displacement required can be altered by using different electrode areas having different sizes. The directional electrode of the present invention may therefore comprise different sized electrode conducting areas which can be used in order to displace the electric field to different degrees.

It may be desirable to have a small electrode conducting area (e.g. less than a sixteenth of the circumference) when it is desired to cause tissue death in a defined area.

As indicated above for the electrode of the first embodiment of the present invention, the electrode conducting area can be any shape. It is also preferred that the longitudinal axis of the one or more electrode conducting areas are parallel or perpendicular to the longitudinal axis of the electrode.

Preferably the one or more electrode areas are rectangular in shape and are about 1.5 to 3 mm in length and 0.2 to 0.5 mm in width.

The core, insulating wires and electrically insulating sheath of the directional electrode are as defined for the electrode according to the first embodiment of the present invention.

As for the first embodiment of the present invention, it is preferred that the electrically conducting material, is gold or platinum.

It is further preferred that the directional electrode of the present invention comprises a mark at the proximal end of the electrode in alignment with the electrode areas for orientating the position of the electrode areas. Preferably the mark is a line along the length of the electrode. The line does not have to be continuous along the length of the electrode and is used by the surgeon in order to be able to determine the position of the electrode conducting areas.

It is preferred that the directional electrode according to the second embodiment of the present invention is a DBS electrode or a deep brain lesioning electrode.

As for the electrode of the first embodiment of the present invention, the directional electrode can be used to produce mono-polar current or bi-polar current.

The directional electrode of the second embodiment of the present invention can be constructed by any method, including the method used to construct the electrode according to the first embodiment of the present invention or via the prior art method comprising welding the electrode conducting areas into place on the electrode.

The present invention further provides a method for constructing the directional electrode according to the second embodiment of the present invention comprising:
coating a core of one or more insulated wires having non-insulated ends with an electrically insulating sheath, wherein the non-insulated ends of the one or more wires are not coated by the sheath; and
depositing electrically conducting material on the surface of the sheath to form the one or more electrode areas which are in electrical contact with a non-insulating end of the one or more insulated wires.

Preferably electrically conducting material is deposited by jet printing, etching, photolithography, plasma deposition, evaporation or electroplating according to the method described in respect of the electrode according to the first embodiment of the present invention.

The present invention also provides the use of the directional electrode of the second embodiment of the present invention for use in therapy. Preferably the therapy is the surgical treatment of abnormalities of brain function, including abnormalities of movement such as Parkinson's disease, Chorea, tremor, multiple sclerosis and cerebral palsy; abnormalities of the mind including depression and obsessive compulsive states, chronic pain syndromes and epilepsy. The directional electrode can also be used to lesion brain tumours, especially in eloquent areas.

In use, the electrode is usually inserted over a supporting wire to provide the required stiffness needed to insert the electrode into the brain of a patient. Alternatively, and provided a plug is not inserted into the end of the electrode, the electrode can be inserted over a guide wire and passed down the guide wire to the desired position.

BRIEF DESCRIPTION OF THE DRAWINGS

Embodiments of the present invention will now be described by way of example only and with reference to the accompanying drawings, in which:

FIG. 3 shows (A) an electrode with protruding non-insulated wire ends, (B) an electrode having electrode conducting areas at one end, (C) an electrode having electrode conducting areas at both ends, (D) a cross section of the end of an electrode having a bung inserted in the end of the electrode.

FIG. 6 shows (A) the distal end of a directional electrode comprising four electrode conducting areas in a staggered arrangement, (B) shows a sectional view of the electrode through line x-x.

DETAILED DESCRIPTION

Example 1

Constructing an Electrode

Figure 1:
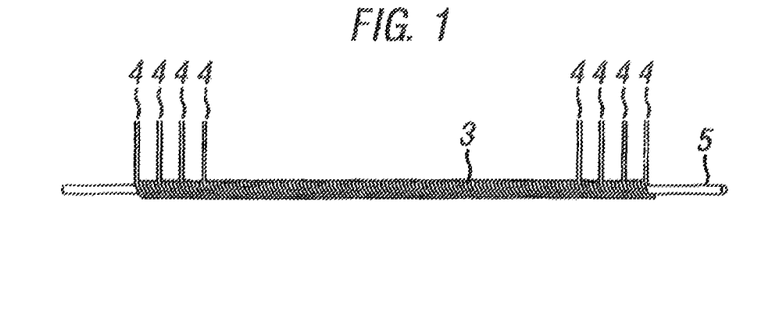
FIG. 1 shows a core of an electrode comprising four insulated wires wound on a tungsten wire support.
Figure 2:
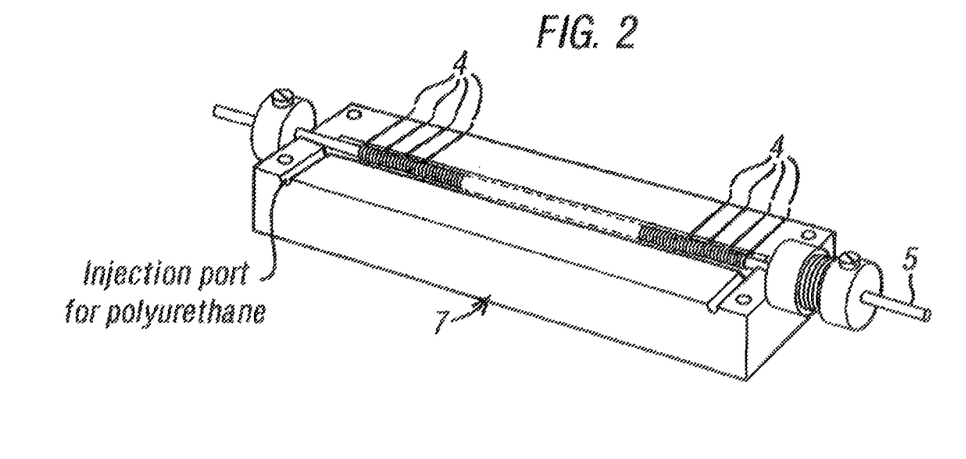
FIG. 2 shows a mould half for producing an insulating sheath around a core.
Figure 3A:
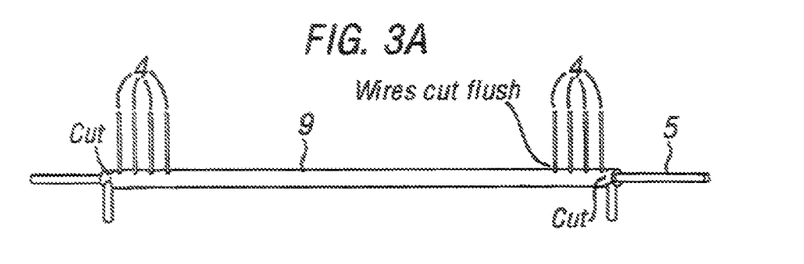

An electrode (1) having a proximal end and a distal end is constructed by winding four platinum/iridium alloy insulated wires (diameter of 0.10 mm) onto a tungsten wire (5) in order to form the structure shown in FIG. 1. Thus the ends of each platinum/iridium wire extend radially away from the tungsten wire and are spaced apart along the length of the tungsten wire. This structure forms the core (3) of the electrode (1). The core (3) is then inserted into a mould (7) and a polyurethane sheath (9) cast around the core (3). The tungsten wire (5) is held under tension in the mould (7). The ends (4) of the insulated wires protrude from the sheath (9) formed around the core (3) and are then cut flush to the surface of the sheath (9). By cutting the ends (4) of the wires so that they are flush to the surface of the sheath (9), the metallic core of the wires will be exposed on the surface of the sheath (see FIG. 3A).

Figure 3B:
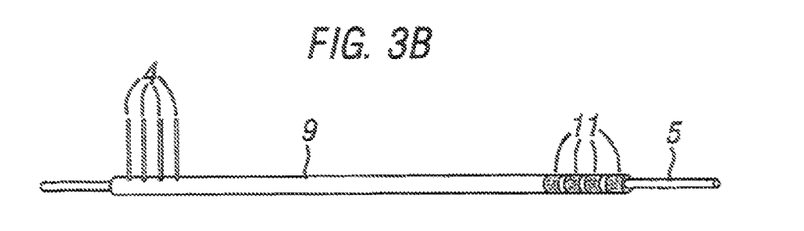
Figure 3C:
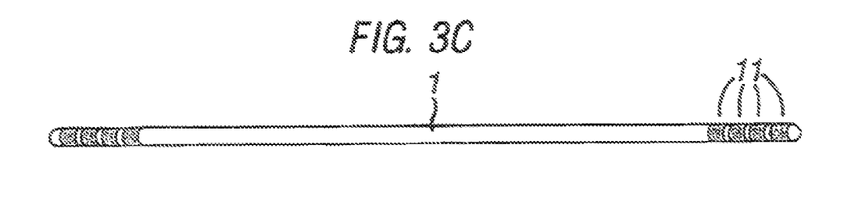

Electrode conducting areas (11) are then formed on the sheath (9) and in contact with the metallic surface of each of the cut wires. The electrically conducting material used is platinum. The platinum is deposited as a ring around the electrode (1) on the sheath (9) of the electrode (1) to form an electrode conducting area (11) as a ring around the electrode (1). FIGS. 3B and C clearly show the formation of the electrode conducting areas (11) on the proximal and distal ends of the electrode (1).

In this example the platinum is deposited by depositing ink on the sheath (9) by lithographic printing thereby forming a seeding layer, and depositing platinum by electroless deposition (see WO 00/33262).

Figure 3D:
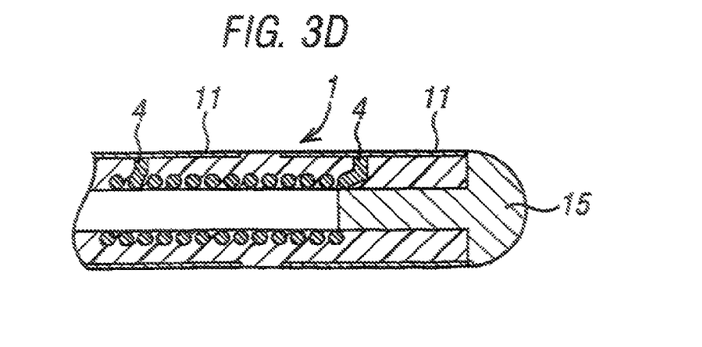

Once the electrode conducting areas (11) are formed on the sheath (9), the tungsten wire (5) is removed and a plug (15) is inserted in the distal end of the electrode (1) (see FIG. 3D).

On inserting the electrode into the brain of a patient, a tungsten wire is inserted into the electrode to provide the electrode with sufficient rigidity for insertion.

In use, the proximal end of the electrode (1) is connected to a pulse generator. The electrode (1) can then be used to produce a mono-polar electrical field or a bipolar electrical field (4) at the distal end of the electrode (1) depending on the electrical contacts made with the generator.

The resulting electrode (1) can be used in a variety of surgical procedures, in particular in a variety of neurosurgical procedures.

Example 2

Method of Constructing a DBS Directional Electrode

Figure 5:
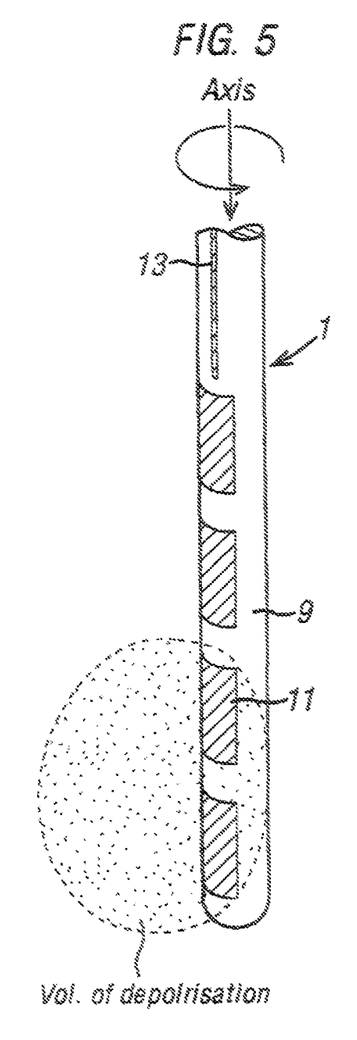
FIG. 5 shows the distal end of a directional electrode comprising four electrode conducting areas arranged in a line.

An electrode (1) is constructed in accordance with the method described in Example 1 except that the platinum material deposited in order to form the electrode conducting areas (11) at the distal end of the electrode is deposited in four discrete rectangles on one side of the electrode (1) (see FIG. 5). Each electrode conducting area (11) is approximately 1.5 mm long and 0.5 mm in width. The width constitutes 45.degree. of the electrode's circumference as the electrode's diameter is 1.27 mm. A gap of 0.5 mm is formed between each electrode conducting area (11). The proximal end of the electrode (1) has electrode conducting areas (11) formed as rings in accordance with the method disclosed in Example 1. The electrode (1) also comprises a line (13) running along the length of the electrode (1) which is aligned with the electrode conducting areas (11) and serves as an indicator of the orientation of the electrode conducting areas (11).

Example 3

Figure 6A:
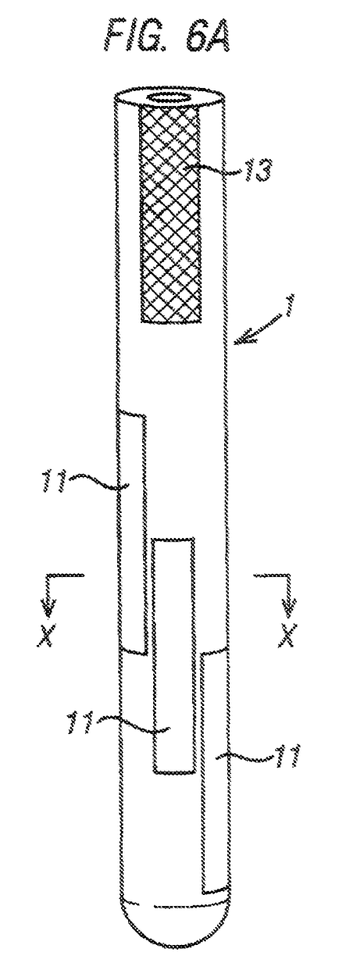
Figure 6B:
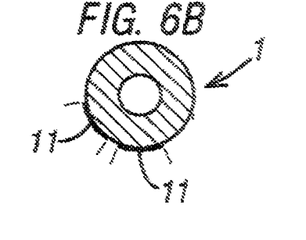

Method of Constructing a DBS Directional Electrode with Staggered Electrode Conducting Areas In another example, the electrode conducting areas (11) are formed at the distal end of the electrode (1) in a staggered arrangement (see FIG. 6A). The electrode conducting areas (11) are about 3 mm in length and 0.5 mm in width and each electrode conducting area (11) is separated from its neighbour by 0.2 mm.

Use of the Directional Electrode

A directional DBS electrode (1) made according to Example 2 or Example 3 is inserted into the brain of a patient so that the distal end of the electrode (1) is placed at the desired target. The target is stimulated to confirm accurate localisation and the electrode (1) is rotated in order to ensure that the optimum position of the electrode conducting areas (11) is obtained. The indicated line (13) on the electrode (1) will assist with this orientation. The DBS electrode (1) is now fixed to the patient's skull and connected to a generator that is implanted subcutaneously in the patient. Generally, the electrode of Example 2 will be used to produce a bipolar electric current and the electrode of Example 3 will be used to produce a monopolar electric current.

If the electrode (1) position proves to be sub-optimal post operatively, then it is possible to try the alternative electrode conducting areas (11) in order to see if the position can be optimised by utilising one of the alternative electrode conducting areas (11).

The directional electrode (1) enables the surgeon to be able to alter the position of producing an electrical current by simply rotating the electrode (1) by utilising other electrode conducting areas (11) formed on the distal end of the electrode (1).

What is claimed is:

1. A method for constructing an implantable medical lead comprising:
    winding one or more insulated wires around a support member to form a core, the one or more insulated wires each having first and second ends and each having a metallic core, wherein the first and second ends of the one or more insulated wires are radially extended from the support member;
    coating the core with an insulating sheath such that the first and second radially extending ends of the one or more insulated wires are not coated by the sheath;
    cutting the one or more insulated wires flush with the sheath to remove the first and second ends such that the metallic cores of the one or more insulated wires are exposed at the surface of the sheath; and
    depositing electrically conducting material on the surface of the sheath such that the electrically conducting material is contacted with the exposed metallic cores of the one or more insulated wires at the surface of the sheath to form one or more electrode areas.

2. The method of claim 1, wherein winding the one or more insulated wires around the support member comprises winding the one or more insulating wires around a tungsten wire.

3. The method of claim 1, wherein depositing the electrically conducting material on the surface of the sheath comprises deposition by a process selected from the group consisting of jet printing, etching, photolithography, plasma deposition, evaporation and electroplating.

4. The method of claim 1, wherein the electrically conducting material is deposited on the surface of the sheath such the one or more electrode areas are formed as directional electrodes.

5. The method of claim 4, wherein the directional electrodes extends over less than half of the circumference of the sheath.

6. The method of claim 1, further comprising removing the support member after the electrically conductive material is deposited on the sheath.

7. A method for constructing an implantable medical lead comprising:
    coating a core comprising one or more insulated wires with an insulating sheath, the one or more insulated wires each having first and second ends and each having a metallic core, the core configured such that the first and second ends of the one or more insulated wires radially extend from the core, wherein the core is coated such that the first and second radially extending ends of the one or more insulated wires are not coated by the sheath;
    cutting the one or more insulated wires flush with the sheath to remove the first and second ends such that the metallic cores of the one or more insulated wires are exposed at the surface of the sheath; and
    depositing electrically conducting material on the surface of the sheath such that the electrically conducting material is contacted with the exposed metallic cores of the one or more insulated wires at the surface of the sheath to form one or more electrode areas.

8. The method of claim 7, wherein the core comprises the one or more insulated wires wound around a support member to produce the core.

9. The method of claim 8, wherein the support member is a tungsten wire.

10. The method of claim 7, wherein depositing the electrically conducting material on the surface of the sheath comprises deposition by a process selected from the group consisting of jet printing, etching, photolithography, plasma deposition, evaporation and electroplating.

11. The method of claim 7, wherein the electrically conducting material is deposited on the surface of the sheath such the one or more electrode areas are formed as directional electrodes.

12. The method of claim 11, wherein the directional electrodes extend over less than half of the circumference of the sheath.

13. The method of claim 11, wherein the directional electrodes extend over less than a quarter of the circumference of the sheath.

14. The method of claim 11, wherein the directional electrodes extend over about an eighth of the circumference of the sheath.

15. The method of claim 7, wherein the electrically conducting material is deposited on the surface of the sheath such the one or more electrode areas have a length of 1.5 mm to 3 mm and a width of 0.2 mm to 0.5 mm.

* * * * *